United States Patent [19]

Shah et al.

[11] Patent Number: 5,674,522
[45] Date of Patent: Oct. 7, 1997

[54] BEVERAGE CONCENTRATE FOR DRUG DELIVERY

[75] Inventors: Manoj N. Shah, Norristown; Warren L. Sunshine, Dresher, both of Pa.

[73] Assignee: McNeil-PPC, Inc., Skillman, N.J.

[21] Appl. No.: 534,085

[22] Filed: Sep. 26, 1995

Related U.S. Application Data

[63] Continuation of Ser. No. 133,551, Oct. 7, 1993, abandoned.

[51] Int. Cl.$^6$ ............................................. A61K 9/14
[52] U.S. Cl. ............................................. 424/439; 424/489
[58] Field of Search ............................ 424/439, 489, 424/466

[56] References Cited

U.S. PATENT DOCUMENTS

| | | | |
|---|---|---|---|
| 4,003,999 | 1/1977 | Lybrand et al. | 424/195 |
| 4,851,252 | 7/1989 | Greither et al. | 426/599 |
| 4,894,233 | 1/1990 | Sharma et al. | 424/440 |
| 5,429,836 | 7/1995 | Fuisz | 426/601 |

OTHER PUBLICATIONS

Fact and Comparisons, Sewester et al., Jan. 1993, pp. 214(a)–214(d).

Physician's Desk Refernce, 13th Ed., Medical Economics Company, Inc., pp. 413, 595–596 & 598–599 (1992).

ADWEEK, Eastern Ed., vol. XXXIII, No. 27, p. 5 (Jul. 6, 1992).

Abstracts from Product Scan (Marketing Intelligence): Comtrex Multi-Symptom Hot Flu Relief, Accession No. 101267 (1992); Comtrex Hot Flu Relief, Accession No. 97807 (1992).

Labeling from Traditional Medicinals, Inc. Gypsy Cold Care®, Smooth Move and Breath Easy® Herbal Tea Products,© 1989.

*Primary Examiner*—Thurman K. Page
*Assistant Examiner*—James M. Spear
*Attorney, Agent, or Firm*—Bernard F. Plantz

[57] ABSTRACT

The present invention relates to a beverage concentrate suitable for delivering orally administrable pharmaceutical actives. The beverage concentrate contains an instant food, the pharmaceutical active, and sweetening and flavoring agents. The concentrate produces a pleasant tasting beverage when dissolved in hot water.

26 Claims, No Drawings

BEVERAGE CONCENTRATE FOR DRUG DELIVERY

This is a continuation of application Ser. No. 08/133,551, filed Oct. 7, 1993 now abandoned.

FIELD OF THE INVENTION

The present invention relates to a beverage concentrate containing one or more pharmaceutical actives, and, more particularly, to a concentrate which is dissolved in hot water to form a pleasant tasting, hot liquid beverage capable of delivering one or more pharmaceutical actives.

BACKGROUND OF THE INVENTION

Hot liquid herbal tea beverages have been used for centuries in early medical practice and folklore to treat a variety of ailments. These beverages are typically prepared by brewing the leaves, stems or roots of plants known to contain therapeutically active compounds. For example, menthol derived from peppermint leaves has been used as a decongestant, sennosides A and B derived from senna leaves have been used as a laxative and ephedrine derived from Ma Huang/ephedra plants has been used as a decongestant.

The brew produced from these plants is often foul tasting, and the delivery of the active ingredient is very imprecise because the active must be leached from the plant material. The imprecise delivery can lead to under- or over-dosing of the active ingredient. Although these herbal tea beverages are in use around the world for their therapeutic effects, lack of dosage uniformity makes them unsuitable for use as a regulated pharmaceutical preparation.

Powdered pharmaceutical preparations containing active ingredients, sweeteners and flavors, which are dissolved in hot water and consumed as a hot liquid medication, are commercially available. These products typically contain acetaminophen, chlorpheniramine maleate, pseudoephedrine hydrochloride and dextromethorphan hydrobromide, and are used to provide temporary relief of the symptoms associated with the common cold and flu. These preparations typically have citrus flavors, such as lemon.

Since the active ingredient is in a powdered form that dissolves in the hot water and is consumed by the user, the dosing problems associated with herbal tea products are avoided. These hot liquid medications have, however, found limited acceptance in the marketplace because they often have an "artificial" taste.

R. A. Lybrand et al. in U.S. Pat. No. 4,003,999, issued Jan. 18, 1977, has suggested the use of aspirin-tea coprecipitates for treating inflammation. The coprecipitates are prepared from solutions of aspirin and instant tea. The coprecipitates can then be formulated into pressed or coated tablets, or they can be encapsulated and formulated into other pharmaceutical dosage forms, such as liquid suspensions and powders. There is, however, no suggestion to dissolve the coprecipitates in hot water so as to form a hot medicated beverage.

A need exists for a hot liquid beverage that is capable of delivering a pharmaceutical active without the dosing problems associated with herbal teas, and which has a taste similar to natural food products.

SUMMARY OF THE INVENTION

The present invention provides a beverage concentrate containing an instant food selected from the group consisting of instant tea, instant coffee, instant soup and instant cocoa, and a therapeutically effective amount of a pharmaceutical selected from the group consisting of antitussives, expectorants, antihistamines, sympathomimetics, analgesics, laxatives, antidiarrheals, and mixtures thereof. The concentrate is dissolved in hot water and orally consumed, so as to deliver the pharmaceutical active to the user.

The present invention overcomes the dosing problems associated with herbal tea products because the pharmaceutical active is present in a powder form, that readily dissolves in the hot water. Further, the food product, such as tea, is in an instant form, rather than a leafy form that may absorb and/or adsorb the pharmaceutical active and thereby affect product dosing.

DETAILED DESCRIPTION OF THE PREFERRED EMBODIMENTS

The present invention provides a beverage concentrate suitable for delivering orally administrable pharmaceutical actives. When the beverage concentrate, containing an instant food and the pharmaceutical, is added to hot water, a hot liquid beverage is formed. Since the concentrate does not contain plant materials, e.g., leaves, stems or roots, normally found in herbal tea medications, the pharmaceutical active is accurately delivered to the user.

The instant food used in the beverage concentrate of the present invention is a food product that forms a pleasant tasting, hot liquid beverage when added to hot water (90° C.). Suitable instant foods available for use in the present invention include commercially available instant tea, instant coffee, instant soup and instant cocoa. As used in the present invention, instant soup also includes commercially available bouillon which forms a liquid broth when dissolved in hot water. Preferred instant foods for use in the present invention include decaffeinated or caffeinated instant coffee and caffeinated or decaffeinated instant black tea. These instant teas and coffees are prepared using conventional techniques, such as spray- or freeze-drying brewed coffee or tea to form a powder that dissolves instantly in hot water.

The pharmaceutical active used in the present invention can be any medication which can be administered orally to transmit the active agent into the gastrointestinal tract and into the bloodstream at therapeutically effective levels. The pharmaceutical should be in a purified powder form, e.g., USP grade, as opposed to the raw plant material, such as senna leaves or ephedra leaves.

Preferred pharmaceutical actives are selected from the group consisting of antitussives, expectorants, antihistamines, sympathomimetics, analgesics, laxatives, antidiarrheals and mixtures thereof. Pharmaceutical used in cold or cough/cold preparations, such as an analgesic combined with one or more of an antitussive, expectorant, antihistamine and sympathomimetic, are especially preferred.

Suitable antitussives for use in the present invention include dextromethorphan, diphenhydramine, pharmaceutically acceptable salts thereof (e.g.,dextromethorphan phan hydrobromide and diphenhydramine hydrochloride), and mixtures thereof. Expectorants which may be used in the invention include guaifenesin. Antihistamines suitable for use in the invention include chlorpheniramine, brompheniramine, terfenadine, astemizole, diphenhydramine, pharmaceutically acceptable salts thereof (e.g., chlorpheniramine maleate, brompheniramine maleate and diphenhydramine hydrochloride), and mixtures thereof. Sympathomimetics suitable for use in the concentrate include pseudoephedrine, phenylpropanolamine, pharmaceutically acceptable salts thereof (e.g., pseudoephedrine hydrochloride), and mixtures thereof. Laxatives which may be used in the beverage concentrate of the present invention include sennosides A and B. Antidiarrheals suitable for use in the concentrate include loperamide and pharmaceutically acceptable salts thereof (e.g., loperamide HCl).

The analgesic used in the present invention includes acetaminophen and non-steroidal anti-inflammatory drugs (NSAIDs). Preferably, the NSAID is selected from the group consisting of propionic acid derivatives, such as ibuprofen, fenoprofen, naproxen and ketoprofen; fenamic acid derivatives, such as meclofenamate and mefenamic acid; oxicams, such as piroxicam; indole acetic acids, such as indomethacin, sulindac and tolmetin; and pharmaceutically acceptable salts thereof.

Additional antitussives, expectorants, antihistamines, sympathomimetics, laxatives, antidiarrheals and analgesics suitable for use in the present invention are described in *Remington's Pharmaceutical Sciences*, Mack Publishing Co., Easton, Pa. 18th ed., Chapters 39, 42, 43, 58 and 59 (1990), which is hereby incorporated by reference.

The pharmaceutical active(s) is present in the beverage concentrate in a therapeutically effective amount, which is an amount that produces the desired therapeutic response upon oral administration, and can be readily determined by one skilled in the art. In determining such amounts, the particular compound being administered, the bioavailability characteristics of the compound, the dose regime, the age and weight of the patient, and other factors must be considered.

In addition to the flavor imparted to the concentrate by the instant food product, a taste-masking composition may also be employed to mask the sometimes bitter taste of the pharmaceutical active employed. Generally, the taste-masking composition contains at least one sweetening agent and at least one flavoring agent. The flavoring and sweetening agents added to the concentrate should be of a type and amount to meet the preferences dictated by the intended consumer, e.g., pediatric or adult.

Sugar sweetening agents for use in the concentrate include sugars, such as monosaccharides, disaccharides and polysaccharides. Sugars suitable for use in the present invention include, but are not limited to, xylose, ribose, glucose, mannose, galactose, fructose, dextrose, sucrose, maltose, partially hydrolyzed starch or corn syrup solids and sugar alcohols, such as sorbitol, xylitol, mannitol, glycerine and combinations thereof. A preferred sugar sweetener is granular sucrose.

Water soluble artificial sweeteners may also be employed in place of or in addition to the aforementioned sugar sweeteners. Examples of suitable artificial sweeteners include, but are not limited to, aspartame, sucralose, cyclamates, saccharin and mixtures thereof.

Suitable flavoring agents include natural and/or artificial flavors, such as mints (e.g., peppermint), menthol, cinnamon, vanilla, natural and/or artificial fruit flavors (e.g., cherry, grape, orange, strawberry, and lemon); taste modifiers, such as citric acid; and combinations of two or more thereof.

The concentrate of the present invention may also include one or more vitamins, minerals and/or mineral salts. Suitable vitamins for use in the invention include Vitamin C in the form of ascorbic acid, vitamins of the B-complex group and mixtures thereof. These vitamins, minerals and/or mineral salts are present in the concentrate at levels in accordance with the U.S. Recommended Dose for Adults (USRDA).

The instant food, sweetening agent(s), and flavoring agent (s) are present in the concentrate in amounts that vary depending upon the desired taste of the hot liquid beverage. The concentrate is generally packaged in a unit dose that is dissolved in six ounces of hot water (90° C.).

In a preferred embodiment, the beverage concentrate of the present invention containing instant tea or coffee comprises from about 0.01 to about 5 weight percent of the pharmaceutical active(s), from about 2 to about 10 weight percent of instant tea or coffee, from about 40 to about 98 weight percent of sugar sweetening agent(s) powdered sucrose), and from about 0.5 to about 10 weight percent of the flavoring agent(s). In a preferred tea beverage concentrate containing a sympathomimetic and, optionally, a vitamin, the composition comprises from about 0.45 to about 0.55 weight percent pseudoephedrine hydrochloride, from about 85 to about 95 weight percent powdered sucrose, NF, from about 1 to about 5 weight percent citric acid, from about 1 to about 5 weight percent lemon flavoring agent(s), from about 2 to about 7 weight percent instant black tea and from 0.5 to about 3 weight percent ascorbic acid (Vitamin C).

In the foregoing embodiments, if an artificial sweetener is used alone or in combination with sugar sweetener(s), the level of the sugar sweetener(s) would be reduced by up to 95% by weight. A concentrate employing an artificial sweetener generally comprises from about 0.05 to about 40 weight percent of the pharmaceutical active(s), from about 10 to about 40 weight percent of instant tea or coffee, from 0 to about 35 weight percent of sugar sweetening agent (powdered sucrose), from about 1 to about 40 weight percent of artificial sweetener and from about 10 to about 50 weight percent of the flavoring agent(s)

Various other pharmaceutically acceptable excipients may be included, such as preservatives and coloring agents, in the concentrate of the present invention.

The concentrate of the present invention is preferably in the form of a quick dissolving dry powder having a U.S. standard mesh size of less than about 20, and preferably between about 30 and about 80.

When preparing the beverage concentrate, the components are combined in a conventional mixing device, such as a twin shell or bin blender, and then dispensed into air-tight packages, such as polypropylene lined foil pouches or other conventional sachets. Conventional pouch filling equipment, such as a dual head Bartlet pouch filling machine, is used to package the concentrate. In order to enhance the flowability of the powdered product, it has been found advantageous to set aside a majority of the sweetening agent, e.g., sucrose, and blend it with the remaining components of the composition during the pouch filling operation.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE I

This Example provides a comparison of the amount of pseudoephedrine HCl delivered from a tea beverage made with a concentrate of the present invention and a control tea beverage prepared by brewing a tea bag containing a like amount of pseudoephedrine HCl.

The tea beverage in accordance with the present invention was prepared by mixing 60 mg of fine granular pseudoephedrine HCl with 450 mg. of instant decaffeinated black tea. This powdered admixture was then added to six ounces of hot water (90° C.) and allowed to stand for two minutes. The beverage was then stirred and transferred to a jar for the pseudoephedrine HCl assay.

The control beverage was prepared by opening a standard tea bag (TETLEY caffeinated brand) and adding 60 mg. of fine granular pseudoephedrine HCl to the tea leaves contained in the bag. The bag was resealed and then immersed in six ounces of hot water (90° C.) for two minutes. The bag was dunked twice and then squeezed over the beverage to remove the excess liquid. The beverage was stirred and transferred to a jar for the pseudoephedrine HCl assay.

Duplicate samples of the inventive and control tea beverages were assayed for pseudoephedrine HCl using high pressure liquid chromatography (HPLC). The HPLC conditions were as follows:

Column: Zorbax SCX 300 25 cm×4.6 mm

Mobile Phase: Acetonitrile: 20 mM potassium phosphate monobasic solution (60:40)

Detector: 220 nm

Flow Rate: 2 mL/min

Injection Volume: 20 μL

Approximate Retention Time for Pseudoephedrine HCl: six minutes

The average results of the two assayed samples of the inventive and control tea beverages are shown below as percent of theoretical value:

Inventive: 104.6±1.7%

Control: 94.2±1.7%

The foregoing results demonstrate that 10% more of the active ingredient was obtained from the tea beverage prepared with the concentrate of the present invention as compared to a tea beverage prepared by brewing a tea bag containing a like amount of the active ingredient. While not wishing to be bound by any theory, applicants believe a proportion of the active ingredient in the control was absorbed and/or adsorbed by the tea leaves and/or the tea bag, whereas the concentrate of the present invention does not contain these foreign substances which may affect the delivery of the active ingredient.

EXAMPLE II

This Example discloses a tea beverage concentrate containing pseudoephedrine and Vitamin C. The ingredients contained in the concentrate are as follows:

| Ingredient | Grams/Unit Dose | Wt. Percent |
| --- | --- | --- |
| Sucrose NF (extra fine granular) | 11.00 | 91.13 |
| Pseudoephedrine HCL | 0.06 | 0.50 |
| Citric Acid USP (Anhydrous) | 0.30 | 2.48 |
| Decaffeinated Instant Black Tea | 0.45 | 3.73 |
| Natural Lemon Flavor | 0.20 | 1.66 |
| Ascorbic Acid USP (ultrafine) | 0.06 | 0.50 |

The ingredients were blended and then packaged in single unit dose foil pouches.

A pleasant tasting hot liquid beverage was prepared by dissolving the contents of one of the pouches in hot water (90°) and then stirring.

Various modifications can be made to the above-described embodiments without departing from the spirit and scope of the present invention.

What is claimed is:

1. A beverage concentrate comprising:
    a hot instant beverage selected from the group consisting of instant coffee and instant cocoa; and
    a therapeutically effective amount of pharmaceutical selected from the group consisting of antitussives, expectorants, antihistamines, sympathomimetics, laxatives, antidiarrheals, and mixtures thereof.

2. The concentrate of claim 1 wherein the antihistamine is selected from the group consisting of chlorpheniramine, brompheniramine, terfenadine, astemizole, diphenhydramine, pharmaceutically acceptable salts thereof, and mixtures thereof.

3. The concentrate of claim 1 wherein the antitussive is selected from the group consisting of dextromethorphan, diphenhydramine, pharmaceutically acceptable salts thereof, and mixtures thereof.

4. The concentrate of claim 1 wherein the sympathomimetic is selected from the group consisting of pseudoephedrine, phenylpropanolamine, pharmaceutically acceptable salts thereof, and mixtures thereof.

5. The concentrate of claim 1 wherein the expectorant is guaifenesin.

6. The concentrate of claim 1 wherein the laxative is sennosides A and B.

7. The concentrate of claim 1 wherein the antidiarrheal is loperamide or a pharmaceutically acceptable salt thereof.

8. The concentrate of claim 1, further comprising an analgesic selected from the group consisting of acetaminophen and non-steroidal anti-inflammatory drugs.

9. The concentrate of claim 1 wherein the instant beverage is instant coffee.

10. The concentrate of claim 9, further comprising at least one sweetening agent.

11. The concentrate of claim 10, further comprising at least one flavoring agent.

12. A beverage concentrate dissolved in water, comprising:
    a hot instant beverage selected from the group consisting of instant coffee, instant soup and instant cocoa; and
    a therapeutically effective amount of pharmaceutical selected from the group consisting of antitussives, expectorants, antihistamines, sympathomimetics, laxatives, antidiarrheals, and mixtures thereof.

13. A powdered beverage concentrate dissolved in water, comprising:
    about 2 to about 10 weight percent of a hot instant beverage selected from the group consisting of instant tea and instant coffee;
    about 0.01 to about 5 weight percent of a pharmaceutical selected from the group consisting of antitussives, expectorants, antihistamines, sympathomimetics, analgesics, laxatives, antidiarrheals, and mixtures thereof;
    about 40 to about 98 weight percent of at least one sugar sweetening agent; and
    about 0.5 to about 10 weight percent of at least one flavoring agent.

14. A powdered beverage concentrate, comprising:
    about 2 to about 10 weight percent of a hot instant beverage selected from the group consisting of instant tea and instant coffee;
    about 0.01 to about 5 weight percent of a pharmaceutical selected from the group consisting of antitussives, expectorants, antihistamines, sympathomimetics, analgesics, laxatives, antidiarrheals, and mixtures thereof;

about 40 to about 98 weight percent of at least one sugar sweetening agent; and about 0.5 to about 10 weight percent of at least one flavoring agent.

15. The concentrate of claim 14 wherein the antihistamine is selected from the group consisting of chlorpheniramine, brompheniramine, terfenadine, astemizole, diphenhydramine, pharmaceutically acceptable salts thereof, and mixtures thereof.

16. The concentrate of claim 14 wherein the antitussive is selected from the group consisting of dextromethorphan, diphenhydramine, pharmaceutically acceptable salts thereof, and mixtures thereof.

17. The concentrate of claim 14 wherein the sympathomimetic is selected from the group consisting of pseudoephedrine, phenylpropanolamine, pharmaceutically acceptable salts thereof, and mixtures thereof.

18. The concentrate of claim 14 wherein the expectorant is guaifenesin.

19. The concentrate of claim 14 wherein the analgesic is selected from the group consisting of acetaminophen and non-steroidal anti-inflammatory drugs.

20. The concentrate of claim 14 wherein the laxative is sennosides A and B.

21. The concentrate of claim 14 wherein the antidiarrheal is loperamide or a pharmaceutically acceptable salt thereof.

22. A powdered beverage concentrate dissolved in water, comprising:

about 2 to about 7 weight percent instant tea;

about 0.45 to about 0.55 weight percent pseudoephedrine or pharmaceutically acceptable salts thereof;

about 85 to about 95 weight percent sucrose;

about 1 to about 5 weight percent citric acid; and about 1 to about 5 weight percent lemon flavoring agent.

23. A powdered beverage concentrate comprising:

about 2 to about 7 weight percent instant tea;

about 0.45 to about 0.55 weight percent pseudoephedrine or pharmaceutically acceptable salts thereof;

about 85 to about 95 weight percent sucrose;

about 1 to about 5 weight percent citric acid; and about 1 to about 5 weight percent lemon flavoring agent.

24. The concentrate of claim 23, further comprising about 0.5 to about 3 weight percent of ascorbic acid.

25. A powdered beverage concentrate dissolved in water, comprising:

about 10 to about 40 weight percent of a hot instant beverage selected from the group consisting of instant tea and instant coffee;

about 0.05 to about 40 weight percent of a pharmaceutical selected from the group consisting of antitussives, expectorants, antihistamines, sympathomimetics, analgesics, laxatives, antidiarrheals, and mixtures thereof;

0 to about 35 weight percent of at least one sugar sweetening agent;

about 1 to about 40 weight percent of at least one artificial sweetener; and about 10 to about 40 weight percent of at least one flavoring agent.

26. A powdered beverage concentrate, comprising:

about 10 to about 40 weight percent of a hot instant beverage selected from the group consisting of instant tea and instant coffee;

0.05 to about 40 weight percent of a pharmaceutical selected from the group consisting of antitussives, expectorants, antihistamines, sympathomimetics, analgesics, laxatives, antidiarrheals, and mixtures thereof;

0 to about 35 weight percent of at least one sugar sweetening agent;

about 1 to about 40 weight percent of at least one artificial sweetener; and about 10 to about 40 weight percent of at least one flavoring agent.

\* \* \* \* \*